United States Patent
Humfeld

(10) Patent No.: US 9,868,638 B2
(45) Date of Patent: *Jan. 16, 2018

(54) METHODS OF MAKING AND PURIFYING CARBON NANOTUBES

(71) Applicant: The Boeing Company, Huntington Beach, CA (US)

(72) Inventor: Keith D. Humfeld, Federal Way, WA (US)

(73) Assignee: THE BOEING COMPANY, Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/602,331

(22) Filed: May 23, 2017

(65) Prior Publication Data

US 2017/0260053 A1    Sep. 14, 2017

Related U.S. Application Data

(63) Continuation of application No. 14/611,734, filed on Feb. 2, 2015, now Pat. No. 9,688,537.

(51) Int. Cl.
| | |
|---|---|
| *C01B 31/02* | (2006.01) |
| *G01N 21/64* | (2006.01) |
| *C01B 32/16* | (2017.01) |
| *C01B 32/17* | (2017.01) |
| *C01B 32/172* | (2017.01) |
| *B82Y 40/00* | (2011.01) |

(52) U.S. Cl.
CPC ......... *C01B 31/0266* (2013.01); *C01B 32/16* (2017.08); *C01B 32/17* (2017.08); *C01B 32/172* (2017.08); *G01N 21/64* (2013.01); *B82Y 40/00* (2013.01); *C01B 2202/02* (2013.01); *Y10S 977/751* (2013.01); *Y10S 977/842* (2013.01); *Y10S 977/845* (2013.01)

(58) Field of Classification Search
CPC .......................... C01B 31/026; C01B 31/0266
See application file for complete search history.

(56) References Cited

PUBLICATIONS

Tsuchiya, Koji, et al. "Laser-Irradiation-Induced Enrichment of Metallic Single-Walled Carbon Nanotubes from As-Synthesized Nanotubes Individually Dispersed in Aqueous Solution." Japanese Journal of Applied Physics 51.10R (2012): 105101.*

(Continued)

*Primary Examiner* — Richard M Rump
(74) *Attorney, Agent, or Firm* — MH2 Technology Law Group LLP

(57) ABSTRACT

In one aspect, methods of making semiconducting single-walled carbon nanotubes are described herein. In some implementations, a method of making semiconducting single-walled carbon nanotubes comprises providing a plurality of semiconducting nanotube seeds including (n,m) nanotube seeds and non-(n,m) nanotube seeds. The method further comprises illuminating the plurality of nanotube seeds with a first laser beam having a first wavelength and a second laser beam having a second wavelength, the second wavelength differing from the first wavelength. The first wavelength corresponds to an absorption maximum for a (n,m) carbon nanotube and the second wavelength corresponds to a photoluminescence emission frequency for the (n,m) carbon nanotube.

9 Claims, 5 Drawing Sheets

(56) References Cited

PUBLICATIONS

McDonald, Timothy, et al. "Separation of Solubilized Single-walled Carbon Nanotubes by Chirality using Laser-assisted Selective Oxidation." Meeting Abstracts. No. 22. The Electrochemical Society, 2006.*

Iwata et al., "Simultaneous Control of Chirality and Growth Position of Single-Walled Carbon Nanotube," Advanced Infocomm Technology (ICAIT), 2013 6th International Conference on, Jul. 2013, 2 pages.

Li et al., "Localized Synthesis of Carbon Nanotube Films on Suspended Microstructures by Laser-Assisted Chemical Vapor Deposition," IEEE Transactions on Nanotechnology, vol. 12, No. 3, May 2013, pp. 352-360.

Ruan et al., "Synthesis of Carbon Nanotubes on Suspending Microstructures by Rapid Local Laser Heating," IEEE Sensors Journal, vol. 11, No. 12, Dec. 2011, pp. 3424-3425.

Yang et al., "Chirality-Specific Growth of Single-Walled Carbon Nanotubes on Solid Alloy Catalysts," Nature, vol. 510, Jun. 2014, 13 pages.

Zhou et al., "Laser-Assisted Nanofabrication of Carbon Nanostructures," Journal of Laser Applications, vol. 24, No. 4, Jul. 2012, 19 pages.

Shoji, Satoru, et al., "Femtosecond laser-assisted photobleaching of single-wall carbon nanotubes," SPIE LASE, International Society for Optics and Photonics, 2012.

McDonald, Timothy, et al., "Separation of Solubilized Single-walled Carbon Nanotubes by Chirality using Laser-assisted Selective Oxidation," Meeting Abstracts No. 22, The Electrochemical Society, 2006.

Tsuchiya, Kohi, et al., "Laser-Irradiation-Induced Enrichment of Metallic Single-Walled Carbon Nanotubes from As-Synthesized Nanotubes Individually Dispersed in Aqueous Solution," Japanese Journal of Applied Physics 51.10R (2012): 105101.

* cited by examiner

METHODS OF MAKING AND PURIFYING CARBON NANOTUBES

CROSS REFERENCE TO RELATED APPLICATIONS

This application is a continuation application of application Ser. No. 14/611,734, filed Feb. 2, 2015, entitled METHODS OF MAKING AND PURIFYING CARBON NANOTUBES, now allowed, which is incorporated herein by reference in its entirety.

FIELD

The present disclosure relates to methods of making and/or purifying carbon nanotubes and, in particular, to selective growth and/or degradation of semiconducting single-walled carbon nanotubes (SWCNTs), such as photoluminescent single-walled carbon nanotubes, to provide a bulk sample or population of nanotubes enriched and/or depleted in carbon nanotubes having one or more predetermined or preselected chiralities.

BACKGROUND

The properties of a single-walled carbon nanotube strongly depend on its geometric structure. This structure is often characterized by identification and enumeration of chiral indices (n,m). The integers n and m denote the number of unit vectors along two directions in the honeycomb crystal lattice of graphene. These indices can be used to determine important parameters of a nanotube, such as whether the nanotube is metallic (n=m), semimetallic (n−m is a multiple of 3), or semiconducting (other values of n−m). Nanotubes having a value of m=0 are generally referred to as zigzag nanotubes, and nanotubes having values of n=m are generally referred to as armchair nanotubes. Nanotubes having values of n and/or m differing from zigzag and armchair nanotubes are generally referred to as being chiral nanotubes.

A wide variety of growth techniques have been developed to make single-walled carbon nanotubes. Each technique generally produces a population of nanotubes having a distribution of (n,m) indices. While a number of these techniques have focused on providing bulk samples of SWCNTs being enriched in one or more preselected chiralities, most or all prior methods present a number of deficiencies. For example, the distribution of chiralities in a bulk sample often depends on growth conditions and thus can show large variations even within the same method. Further, some prior methods have been unable to provide high ratios of a desired chirality in a bulk sample. In order to remedy these deficiencies, a number of techniques have been devised to purify SWCNT samples by removing SWCNTs having one chirality or another in a post-growth step. Unfortunately, such approaches generally increase process time, increase process costs, and/or result in a relatively low yield of nanotubes of the desired chirality relative to the size of the unpurified bulk sample. Further, such purification techniques may be incapable of providing a bulk sample enriched in a small number of desired chiralities, such as a bulk sample enriched in as few as one or two desired chiralities. Thus, there is a need for improved methods for making and/or purifying semiconducting single-walled carbon nanotubes.

SUMMARY

Methods of making and/or purifying a bulk sample or population of semiconducting single-walled carbon nanotubes, such as photoluminescent carbon nanotubes, are described herein. It is to be understood that methods described herein can be used to selectively heat, grow, and/or degrade or decompose semiconducting single-walled carbon nanotubes or nanotube seeds. For example, in some implementations described further hereinbelow, methods described herein comprise providing a plurality of semiconducting nanotube seeds including nanotube seeds with a predetermined or preselected chirality as well as nanotube seeds with a different chirality than that which has been predetermined or preselected. In some cases, such plurality of semiconducting nanotube seeds can be illuminated with a plurality of laser beams having wavelengths that have been preselected or predetermined in order to effect selective heating, growth, and/or degradation of the selected nanotube seeds and/or any nanotubes that may be formed from such nanotube seeds. The laser beams, in some instances, can be directed toward nanotubes and/or nanotube seeds simultaneously or substantially simultaneously. Further, in some cases, illumination of the plurality of nanotube seeds can selectively heat the nanotube seeds having the desired chirality into a carbon nanotube growth regime. Such selective heating can be performed in a manner such that the carbon nanotube seeds having a chirality other than that which is preselected or predetermined are not heated into the carbon nanotube growth regime and are, therefore, not grown or are grown at a reduced rate relative to the nanotubes having the predetermined or preselected chirality. In this manner, methods described herein can be used to grow a population of nanotubes having a preselected chirality or a plurality of preselected chiralities. Alternatively, in other implementations, selective heating can be performed in a manner such that the carbon nanotube seeds having the predetermined or preselected chirality are heated out of a carbon nanotube growth regime and into a no growth regime, while remaining nanotube seeds having a chirality other than the predetermined or preselected chirality remain in a carbon nanotube growth regime. In this manner, methods described herein can be used to grow a population of nanotubes depleted or substantially depleted in a preselected chirality or plurality of preselected chiralities.

Additionally, in some cases, a population of previously grown carbon nanotubes can be selectively depleted of nanotubes having one or more preselected or predetermined chiralities. For example, in some implementations, a population of carbon nanotubes can be illuminated with a plurality of laser beams having wavelengths that have been preselected or predetermined in order to effect selective heating and/or degradation of nanotubes of a preselected or predetermined chirality. Thus, in some cases, methods described herein can be used to purify a population of semiconducting single-walled carbon nanotubes by selectively degrading nanotubes of a single predetermined or preselected chirality or nanotubes having multiple predetermined or preselected chiralities.

In some instances, a method of making semiconducting single-walled carbon nanotubes comprises forming a plurality of semiconducting nanotube seeds including (n,m) nanotube seeds and non-(n,m) nanotube seeds, and illuminating the plurality of nanotube seeds with a first laser beam having a first wavelength and a second laser beam having a second wavelength, the second wavelength differing from the first wavelength. In some implementations, the first wavelength corresponds to an absorption maximum of a (n,m) carbon nanotube. Further, in some cases, the second wavelength corresponds to a photoluminescence emission frequency of the (n,m) carbon nanotube, such as a peak emission frequency.

Moreover, methods described herein can further comprise selectively heating the (n,m) nanotube seeds. In some implementations, the (n,m) nanotube seeds are selectively heated into a carbon nanotube growth regime from a non-growth or no growth regime. In certain instances, selectively heating the (n,m) nanotube seeds can increase the temperature of the (n,m) nanotube seeds by at least 50° C. Additionally, in some cases, methods described herein further comprise forming a plurality of (n,m) carbon nanotubes from the (n,m) nanotube seeds. In some such implementations, the (n,m) carbon nanotubes formed by the method comprise at least 90% by mass, at least 95% by mass, or at least 99% by mass of the total amount of the carbon nanotubes formed.

In other implementations, methods described herein comprise selectively heating (n,m) nanotube seeds above an upper growth threshold temperature into a carbon nanotube no growth regime. In some instances, selectively heating the (n,m) nanotube seeds in this manner can increase the temperature of the (n,m) nanotube seeds by at least 50° C. Additionally, in some such cases, non-(n,m) nanotube seeds are not heated into a no growth regime but instead remain in a growth regime. Moreover, in some implementations, methods described herein further comprise fainting a plurality of non-(n,m) carbon nanotubes from the non-(n,m) nanotube seeds. In some such implementations, the non-(n,m) carbon nanotubes formed by the method comprise at least 90% by mass, at least 95% by mass, or at least 99% by mass of the total amount of the carbon nanotubes formed.

In another aspect, methods of purifying a population of carbon nanotubes, such as a population of semiconducting SWCNTs, are described herein. In some implementations, methods described herein comprise providing a population of carbon nanotubes including semiconducting (n,m) carbon nanotubes and non-(n,m) carbon nanotubes. The methods further comprise illuminating the population of carbon nanotubes with a first laser beam having a first wavelength and a second laser beam having a second wavelength, the second wavelength differing from the first wavelength. In some implementations, the first wavelength corresponds to an absorption maximum for one or more of the (n,m) carbon nanotubes. Further, in some cases, the second wavelength corresponds to a photoluminescence emission frequency for the one or more (n,m) carbon nanotubes.

Additionally, in some cases, methods of purifying a population of carbon nanotubes further comprise selectively heating the (n,m) carbon nanotubes into a carbon nanotube degradation regime. In some such implementations, the non-(n,m) carbon nanotubes are not heated into the carbon nanotube degradation regime. In certain cases, the (n,m) nanotubes are selectively heated to increase the temperature of the (n,m) nanotubes by at least 50° C. Further, in some instances, methods of purifying a population of carbon nanotubes degrades at least 50% by mass, at least 60% by mass, or at least 75% by mass of the (n,m) carbon nanotubes present in the population.

In still another aspect, compositions are described herein. In some implementations, compositions described herein are enriched or are substantially enriched in semiconducting SWCNTs having one or more predetermined or preselected chiralities. For example, a composition described herein can, in some cases, comprise or include at least 90% by mass, at least 95% by mass, at least 99% by mass, or at least 99.9% by mass of semiconducting SWCNTs having one or more predetermined or preselected chiralities. The nanotubes having one or more predetermined or preselected chiralities in which the sample can be enriched can be selected from nanotubes having (n,m) values selected from the group consisting of (10,3), (9,4), (8,6), (12,1), (11,3), (8,7), (10,5), (9,7), (13,2), (12,4), (11,4), (10,6), (9,8), (11,6), (14,1), (13,3), (12,5), (11,7), (10,8), (15,1), (14,3), (13,5), (10,9), (12,7), (16,2), (15,4), (15,2), (14,4), (13,6), (12,8), (11,9), (14,6), (17,1), (16,3), (15,5), (14,7), (11,10), (13,8), and (13,9).

Moreover, in some implementations, compositions described herein are depleted or substantially depleted in nanotubes having one or more predetermined or preselected chiralities. For example, a composition described herein can, in some cases, comprise or include less than 50% by mass, less than 40% by mass, less than 30% by mass, less than 15% by mass, less than 10% by mass, less than 5% by mass, less than 1% by mass, or less than 0.01% by mass of SWCNTs having one or more predetermined or preselected chiralities. The nanotubes having one or more predetermined or preselected chiralities in which the sample can be depleted can be selected from nanotubes having (n,m) values selected from the group consisting of (10,3), (9,4), (8,6), (12,1), (11,3), (8,7), (10,5), (9,7), (13,2), (12,4), (11,4), (10,6), (9,8), (11,6), (14,1), (13,3), (12,5), (11,7), (10,8), (15,1), (14,3), (13,5), (10,9), (12,7), (16,2), (15,4), (15,2), (14,4), (13,6), (12,8), (11,9), (14,6), (17,1), (16,3), (15,5), (14,7), (11,10), (13,8), and (13,9).

These and other implementations are described in more detail in the detailed description which follows.

DETAILED DESCRIPTION

Figure 1:
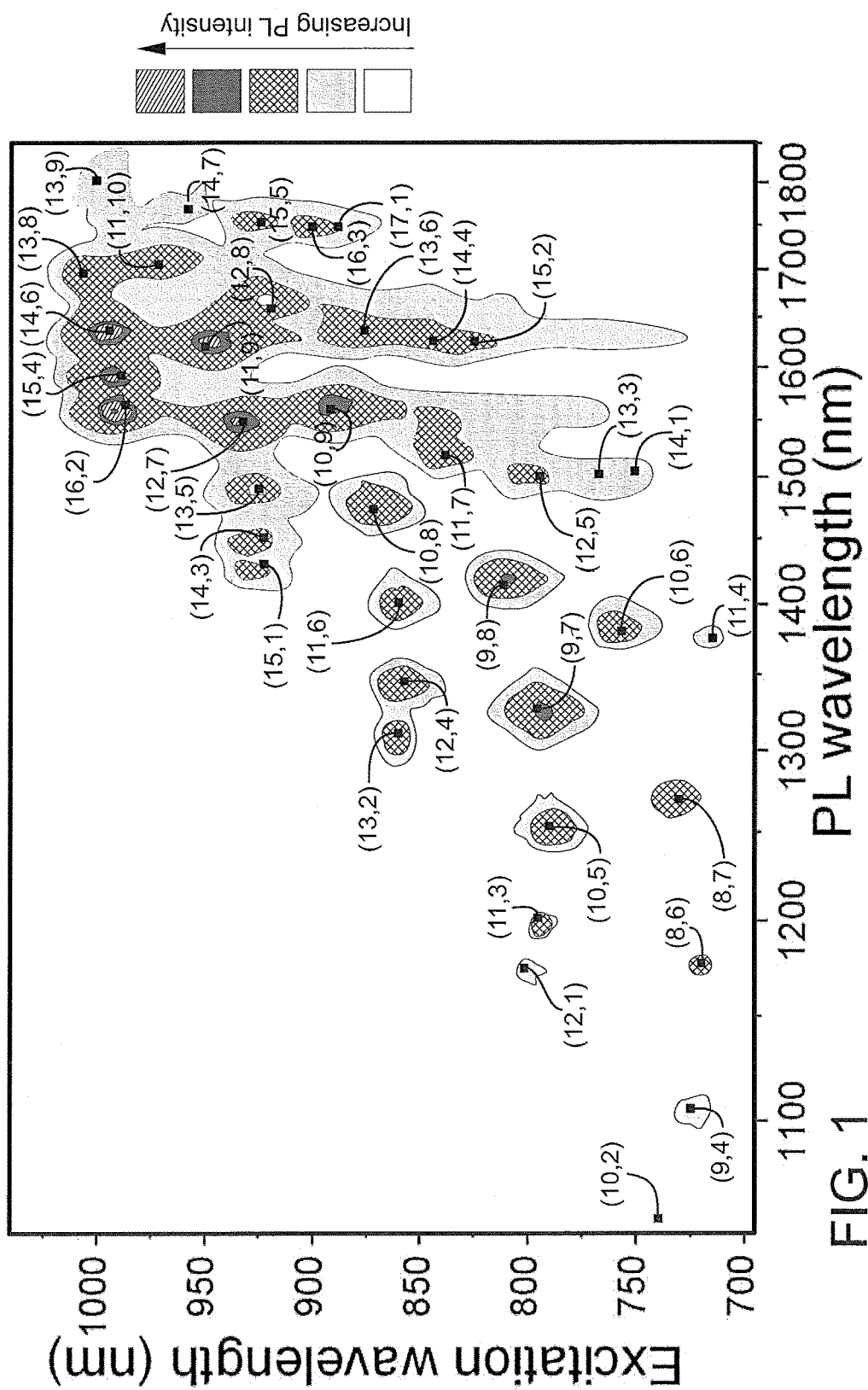
FIG. 1 illustrates a photoluminescence map of single-walled carbon nanotubes.

Implementations described herein can be understood more readily by reference to the following detailed description, examples, and drawings. Elements, apparatus, and methods described herein, however, are not limited to the specific implementations presented in the detailed description, examples, and drawings. It should be recognized that these implementations are merely illustrative of the principles of the present disclosure. Numerous modifications and adaptations will be readily apparent to those of skill in the art without departing from the spirit and scope of the disclosure.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Methods of Making Semiconducting Single-Walled Carbon Nanotubes

A. General

In one aspect, methods of making semiconducting single-walled carbon nanotubes (SWCNTs) are described herein. In some implementations, methods of making semiconducting SWCNTs comprise framing or providing a plurality of semiconducting nanotube seeds including (n,m) nanotube seeds and non-(n,m) nanotube seeds. An "(n,m) nanotube" or an "(n,m) nanotube seed," for reference purposes herein, is a semiconducting nanotube or semiconducting nanotube seed having predetermined or preselected integer values for n and m, respectively. Further, an (n,m) nanotube may be a nanotube formed from an (n,m) nanotube seed having the same values of n and m, respectively. Thus, as used herein, the term "(n,m) nanotube" or "(n,m) nanotube seed" is intended to identify a specific set of (n,m) values, though it is to be understood that the specific (n,m) values can correspond to any desired semiconducting SWCNT or SWCNT seed. Similarly, a "non-(n,m) nanotube" or a "non-(n,m) nanotube seed," for reference purposes herein, is a nanotube or nanotube seed having an (n,m) chirality wherein an integer value of at least one of n or m differs from the integer values of n and m selected to correspond to the (n,m) nanotube or (n,m) nanotube seed.

Further, any nanotube seeds not inconsistent with the objectives of the present disclosure may be used. For example, nanotube seeds may comprise or include a hydrocarbon containing molecule or particle, such as a molecule or particle having a graphenic or tubular fullerene structure, upon which or from which a semiconducting SWCNT can be formed. In some implementations, for instance, a nanotube seed can be a tubular or oblate fullerene nanoparticle having an aspect ratio of less than or equal to about 20:1, less than or equal to about 15:1, or less than or equal to about 10:1. Further, a nanotube seed can be a tubular fullerene nanoparticle having a length of less than or equal to about 20 nm, less than or equal to about 15 nm, or less than or equal to about 10 nm. Additionally, in some cases, nanotube seeds can comprise or consist of template or seed molecules from which a SWCNT can be formed. Such seed or template molecules can be provided or formed in a manner consistent with the description provided by Sanchez-Valencia et al., "Controlled synthesis of single-chirality carbon nanotubes," *Nature* 512 (2014), 61-64. More generally, the plurality of nanotube seeds can be formed using any apparatus and/or by any means or methods not inconsistent with the objectives of the present disclosure. For example, in some implementations, a plurality of semiconducting nanotube seeds is formed from at least one technique selected from the group consisting of catalyst assisted chemical vapor deposition (CVD), high-pressure CO gas decomposition, arc discharge, laser ablation, and direct injection pyrolytic synthesis.

Methods described herein further comprise illuminating the plurality of nanotube seeds with a first laser beam having a first wavelength and a second laser beam having a second wavelength, the second wavelength differing from the first wavelength. In some implementations, the laser beam wavelengths are selected to correspond to one or more optical properties of a desired and/or preselected or predetermined carbon nanotube. For example, in some implementations, the first wavelength corresponds to an absorption maximum for a (n,m) carbon nanotube. Further, in some implementations, the second wavelength corresponds to a photoluminescence emission frequency for the (n,m) carbon nanotube, such as a photoluminescence emission peak. Not intending to be bound by theory, it is believed that the use of such wavelengths can create resonance between two or more energy states in a carbon nanotube or nanotube seed. For instance, resonance may be created between an energy state corresponding to an absorption maximum or peak and an energy state corresponding to a photoluminescence emission peak of the carbon nanotube or carbon nanotube seed. Again not intending to be bound by theory, it is believed that selective heating of predetermined or preselected (n,m) carbon nanotubes or (n,m) nanotube seeds can be achieved in this manner.

In some implementations, absorption maxima and/or photoluminescence emission frequencies can be obtained or determined from a photoluminescence map. FIG. 1 illustrates an example of one such map which may be appropriate for use in some implementations of a method described herein. Photoluminescence maps consistent with the present disclosure can be, in some implementations, prepared or created consistent with the methods discussed in Iakoubovskii et al., "IR-extended photoluminescence mapping of single-wall and double-wall carbon nanotubes," *Journal of Physical Chemistry B* 110 (2006), 17420-17424. In photoluminescence maps consistent with the foregoing, a data point is provided which corresponds to a plot of excitation wavelength for an absorption maximum of a nanotube having a given chirality versus the nanotube's photoluminescence wavelength. In FIG. 1, n and m values associated with a particular photoluminescence emission frequency and an absorption maximum are indicated beneath the corresponding data point for that chirality.

In addition, as described further hereinbelow, it is also possible to selectively heat nanotubes having more than one (n,m) value, including in a simultaneous or sequential manner. In such implementations where multiple (n,m) carbon nanotubes or (n,m) nanotube seeds are preselected for selective growth and/or heating, additional laser beams with differing wavelengths can be used. For example, in the event that two (n,m) carbon nanotubes or (n,m) nanotube seeds are preselected to correspond to laser beam wavelengths for illumination, a third laser beam having a third wavelength and a fourth laser beam having a fourth wavelength can be used, the fourth wavelength differing from the third wavelength. The third wavelength, in some implementations, corresponds to an absorption maximum for a second (n,m) carbon nanotube. Further, in some cases, the fourth wavelength corresponds to a photoluminescence emission frequency for the second (n,m) carbon nanotube. Moreover, it is also possible to selectively heat carbon nanotubes having more than two different sets of (n,m) values. For example, in implementations wherein three or more (n,m) nanotubes or (n,m) nanotube seeds are preselected, an additional pair of lasers beams can be used for each added (n,m) nanotube or (n,m) nanotube seed. In some such implementations, the individual wavelengths of each of the additional laser beams can correspond to an absorption maximum or a photoluminescence emission frequency of the desired or preselected (n,m) carbon nanotube. Stated otherwise, 2x laser beams can be used, with x representing an integer value for the number of preselected chiralities.

Laser beams used to illuminate carbon nanotubes and/or carbon nanotube seeds according to methods described herein can comprise any type of laser beam and can have any power and line width not inconsistent with the objectives of the present disclosure. For example, in some cases, a laser beam has a power of about 1 to 10 W/mm$^2$, about 1 to 8 W/mm$^2$, about 1 to 5 W/mm$^2$, about 1 to 4 W/mm$^2$, about 2 to 8 W/mm$^2$, or about 2 to 5 W/mm$^2$. Additionally, in some implementations, a laser beam described herein comprises a continuous wave (CW) or pulsed laser beam having a full-width at half maximum (FWHM) of about 10 nm or less, about 5 nm or less, or about 1 nm or less. Moreover, it is to be understood that the average wavelength of a laser beam described herein may or may not correspond exactly to an optical feature of a carbon nanotube or carbon nanotube seed described hereinabove. In some cases, for example, the average wavelength of a laser beam selected to correspond to an absorption maximum of a carbon nanotube may be within about 5 nm, within about 10 nm, or within about 20 nm of the absorption maximum.

As described further hereinbelow in Sections I.B. and I.C., methods described herein can be used to make a population of carbon nanotubes that is selectively enriched or selectively depleted in carbon nanotubes of one or more desired or preselected chiralities.

Figure 2A:
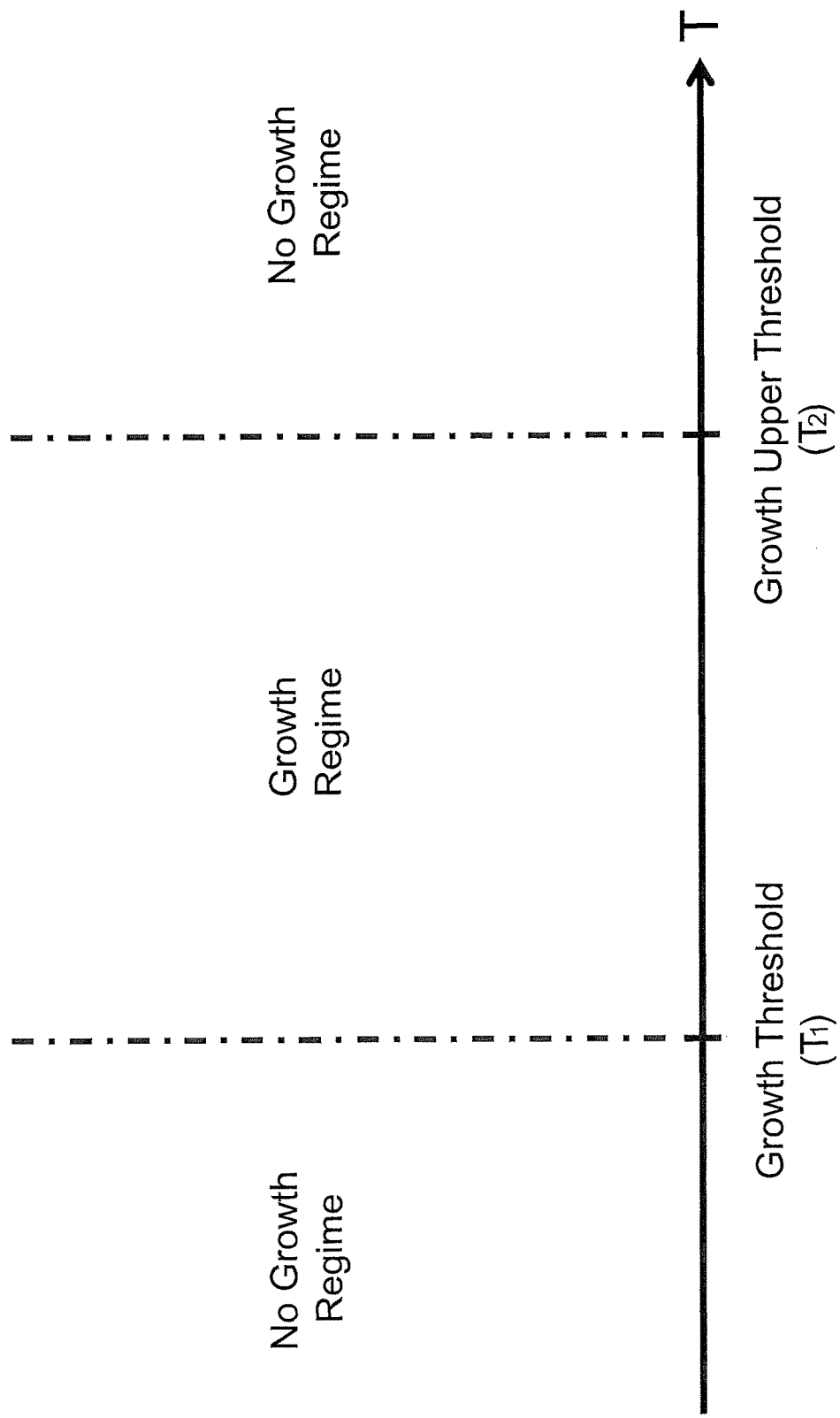
FIG. 2A illustrates a chart of carbon nanotube seed growth and no growth regimes as a function of temperature.

B. Methods of Making a Population of Semiconducting SWCNTs Selectively Enriched in (n,m) Nanotubes In some cases, methods described herein can be used to make a population of semiconducting SWCNTs selectively enriched in (n,m) nanotubes. Such methods, in some implementations, comprise forming a plurality of (n,m) carbon nanotubes from the (n,m) nanotube seeds described in Section IA above. Formation of the (n,m) carbon nanotubes can be carried out by any methods or utilizing any apparatus not inconsistent with the objectives of the present disclosure. For example, in some implementations, forming a plurality of (n,m) carbon nanotubes is performed by selectively heating the (n,m) nanotube seeds into a carbon nanotube growth regime. FIG. 2A illustrates a chart of nanotube growth and no growth regimes as a function of temperature. Consistent with FIG. 2A, a carbon nanotube growth regime, in some implementations, comprises or consists of temperatures at or above a lower growth threshold temperature ($T_1$) but below an upper growth threshold temperature ($T_2$). A lower growth threshold temperature ($T_1$) can be a temperature at or above which carbon nanotube growth occurs (for a given set of experimental conditions) or at or above which carbon nanotube growth proceeds at an increased rate. For example, in some cases, carbon nanotubes at or above $T_1$ may grow up to 1000 times faster, up to 100 times faster, up to 50 times faster, up to 20 times faster, up to 10 times faster, or up to 5 times faster than the growth rate of the carbon nanotubes below $T_1$ or above $T_2$. Thus, below $T_1$, carbon nanotube growth can be substantially reduced or eliminated, such that the graphenic materials are in a "no growth" or reduced growth regime. An upper growth threshold temperature ($T_2$) can be a temperature at or above which carbon nanotubes form defects or do not grow into nanotubes (again, for a given set of experimental conditions). For example, in some cases, up to 100%, up to 90%, up to 80%, up to 70%, up to 60%, or up to 50% of (n,m) carbon nanotube seeds do not grow into carbon nanotubes when exposed to a temperature of $T_2$ or greater. In some implementations, $T_1$ may be a temperature between about 350° C. and about 450° C. or between about 550° C. and about 650° C. In some instances, $T_2$ may be a temperature between about 500° C. and about 600° C. or between about 700° C. and about 800° C. As understood by one of ordinary skill in the art, however, the temperature at which a specific population of carbon nanotubes or carbon nanotube seeds may or may not grow at a specific rate can be dependent on the experimental conditions used.

In some implementations described herein, selectively heating (n,m) nanotube seeds comprises increasing the temperature of the (n,m) nanotube seeds by at least about 40° C., at least about 50° C., or at least about 60° C. In some cases, the temperature of the (n,m) nanotube seeds is increased by about 40-150° C., about 50-100° C., about 50-90° C., or about 50-80° C. Moreover, in some implementations, prior to selectively heating the (n,m) nanotube seeds in a manner described herein, a method comprises reducing the temperature of the (n,m) nanotube seeds below a growth threshold temperature described above, such as $T_1$. For example, in some instances, a plurality of semiconducting nanotube seeds including (n,m) nanotube seeds and non-(n,m) nanotube seeds are formed, and the temperature of the (n,m) nanotube seeds and the non-(n,m) nanotube seeds is subsequently reduced below a growth threshold temperature, prior to selectively heating the (n,m) nanotube seeds, such as into a carbon nanotube growth regime. In such implementations, for instance, a reaction chamber and/or seed gas used to carry out the method may be held at a temperature below a lower growth threshold ($T_1$) such that the (n,m) nanotube seeds are selectively heated into the growth regime, while non-(n,m) nanotube seeds are not heated into the carbon nanotube growth regime. Upon completion of selective heating and/or growth in this manner, certain implementations of methods described herein can result in a bulk sample comprising (n,m) carbon nanotubes and non-(n,m) nanotube seeds. For instance, in some cases, the bulk sample comprises at least 60%, at least 70%, at least 80%, at least 90%, at least 95%, or at least 99% by mass (n,m) carbon nanotubes, based on the total mass of the carbon nanotubes formed by the method.

It is also possible, in some instances, to further purify a bulk sample formed by a method described herein. For example, in some implementations, a method described herein further comprises carrying out one or more steps to separate (n,m) carbon nanotubes from non-(n,m) nanotube seeds. Such separation can be performed by any means, methods, or apparatus not inconsistent with the objectives of the present disclosure. For example, in some implementations, separation can be carried out utilizing nanotube-substrate registration effects, as described by Picconatto et al., "Toward the Bulk, Chiral Separation of Carbon Nanotubes: Experimental Confirmation of Nanotube-Substrate Registration Effects," Mitre (September 2008). In certain other implementations, separation can be carried out by gel chromatography, such as described by Tanaka et al., "From metal/semiconductor separation to single-chirality separation of single-wall carbon nanotubes using gel," *Physica Status Solidi (RRL)-Rapid Research Letters* 5 (2011), 301-306. Other separation methods may also be used.

As described herein, methods according to the present disclosure can be used to selectively grow SWCNTs having a desired set of (n,m) values. However, in some instances, it is possible that not all of the non-(n,m) nanotube seeds are limited to a no growth regime. Thus, in some cases, methods described herein further comprise forming a plurality of non-(n,m) carbon nanotubes from the non-(n,m) nanotube seeds. In such implementations, it may be desirable to deplete, reduce, or eliminate the non-(n,m) nanotubes. In some such instances, methods described herein further comprise illuminating the plurality of nanotubes with a third laser beam having a third wavelength and a fourth laser beam having a fourth wavelength, the fourth wavelength differing from the third wavelength. In some implementations, the third wavelength corresponds to an absorption maximum for the non-(n,m) carbon nanotubes and the fourth wavelength corresponds to a photoluminescence emission frequency for the non-(n,m) carbon nanotubes. Wavelengths utilized for illumination of the plurality of nanotubes can be selected by any means or in any manner not inconsistent with the objectives of the present disclosure. For example, wavelengths can be selected consistent with the above disclosure pertaining to the selection of wavelengths for the illumination of the plurality of nanotube seeds. Further, it is to be understood that the utilization of a "third laser beam" and a "fourth laser beam" in order to illuminate the plurality of nanotubes for the purpose of selectively reducing or degrading certain nanotubes, such as non-(n,m) carbon nanotubes, is to be distinguished from the above-referenced "third laser beam" and "fourth laser beam" for use in illumination of the plurality of nanotube seeds, and that any number of laser beams not inconsistent with the objectives of the present disclosure can be used. For example, some implementations can comprise illumination of the nanotube seeds with y laser beams (such as y=4 to selectively grow carbon nanotubes having two differing sets of (n,m) values). Thus, to also selectively degrade or decompose non-desired carbon nanotubes, such methods can comprise using a total of at least y+2 laser beams.

Figure 2B:
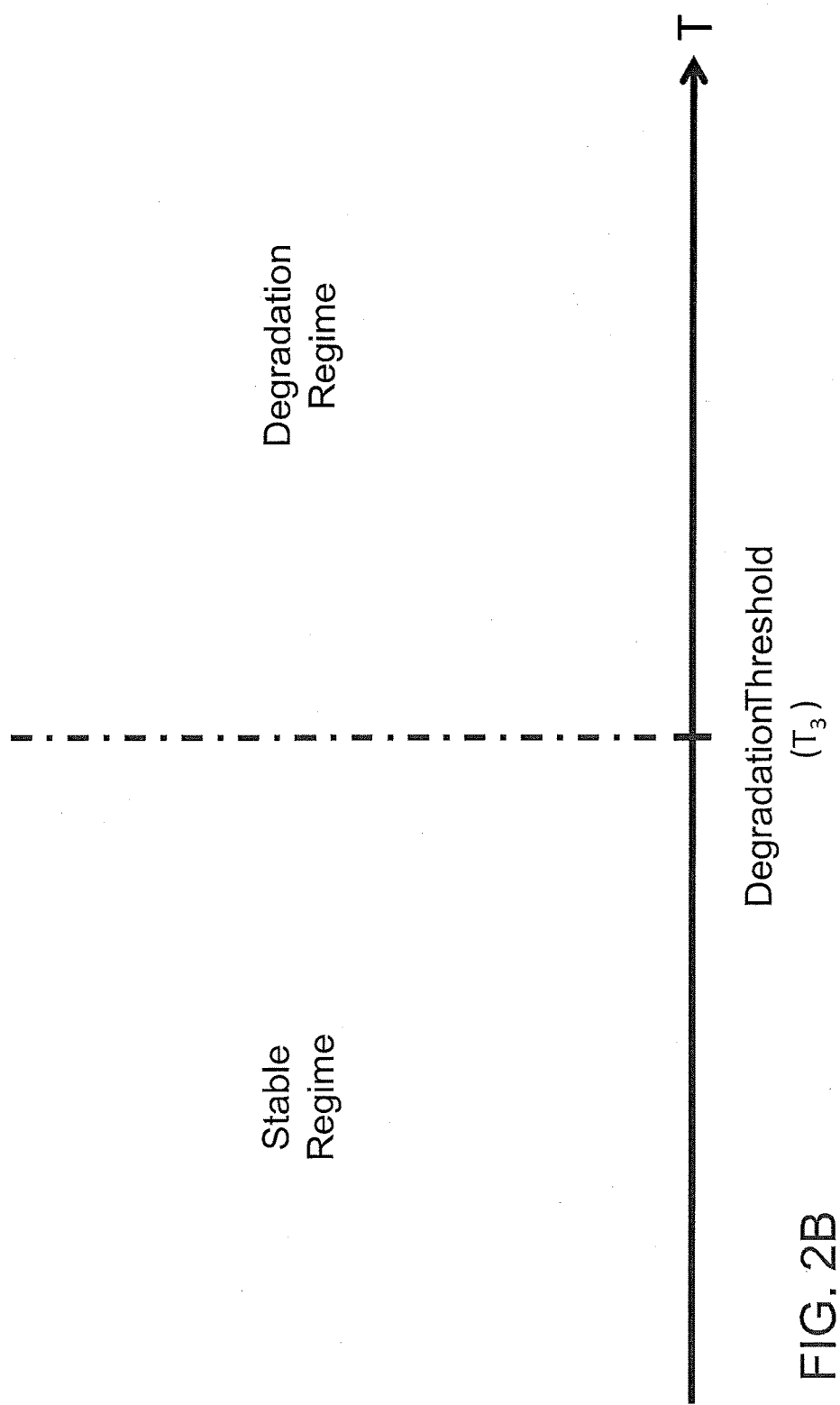
FIG. 2B illustrates a chart of carbon nanotube stability and degradation regimes as a function of temperature.

Thus, in some implementations, methods comprising the formation of a plurality of non-(n,m) carbon nanotubes can further comprise selectively heating the non-(n,m) carbon nanotubes into a carbon nanotube degradation regime. FIG. 2B illustrates a stable regime and a degradation regime of carbon nanotubes as a function of temperature. FIG. 2B also illustrates a degradation threshold temperature ($T_3$) dividing these regimes. A degradation threshold temperature ($T_3$) can be a temperature at or above which carbon nanotubes form defects, degrade, and/or decompose (again, for a given set of experimental conditions). For example, in some cases, up to 100%, up to 90%, up to 80%, up to 70%, up to 60%, or up to 50% of carbon nanotubes can decompose when exposed to a temperature of $T_3$ or greater, including for a time period of up to 5 seconds, up to 10 seconds, up to 30 seconds, up to 1 minute, or up to 5 minutes. A stable regime, therefore, is a temperature below $T_3$ at which carbon nanotubes remain substantially free of defects, degradation and/or decomposition. For example, in some cases, less than 50% of carbon nanotubes form defects, degrade, and/or decompose below $T_3$, such as less than about 40%, less than about 30%, less than about 20%, less than about 10%, or less than about 5% of carbon nanotubes. In some cases, a stable regime can include a carbon nanotube growth regime and/or a carbon nanotube no growth regime. For example, in some instances, a stable regime can include temperatures $T_1$ and $T_2$ from FIG. 2A. Further, in some implementations, $T_3$ may be a temperature between about 400° C. and about 500° C. As understood by one of ordinary skill in the art, however, the temperature at which a specific population of carbon nanotubes or carbon nanotube seeds may or may not form defects, degrade, and/or decompose can be dependent on the environmental and/or experimental conditions used. Moreover, in some implementations, environmental or experimental conditions can be changed prior to selective heating into a carbon nanotube degradation regime. For example, in implementations wherein growth occurs in an oxygen-free or substantially oxygen-free atmosphere, selective heating into a degradation regime can be performed in air or in an atmosphere including oxygen or some other chemically active atmosphere conducive to degradation of carbon nanotubes at a relatively low temperature.

In some cases, selectively heating the non-(n,m) carbon nanotubes increases the temperature of the non-(n,m) carbon nanotubes by at least about 40° C., at least about 50° C., or at least about 60° C. In some cases, the temperature of the non-(n,m) carbon nanotubes is increased by about 40-150° C., about 50-100° C., about 50-90° C., or about 50-80° C. In certain cases, selectively heating the non-(n,m) carbon nanotubes can be performed in order to degrade or decompose a substantial portion of the non-(n,m) carbon nanotubes. Reduction of a substantial portion of the non-(n,m) carbon nanotubes can comprise or include degradation or decomposition of at least 50% by mass of the non-(n,m) carbon nanotubes, at least 60% by mass of the non-(n,m) carbon nanotubes, or at least 75% by mass of the non-(n,m) carbon nanotubes. In some instances, about 50-100%, about 50-99%, about 50-90%, about 60-95%, about 60-90%, about 60-80%, about 70-99%, about 70-90%, about 80-99%, or about 90-100% by mass of the non-(n,m) carbon nanotubes are degraded or decomposed. Additionally, it is to be understood that selective heating of the non-(n,m) carbon nanotubes can be performed to reduce or deplete carbon nanotubes having any number of predetermined or preselected non-(n,m) chiralities, and that such reduction or depletion can be carried out by utilizing additional laser beams and/or by selective heating of the carbon nanotubes having the predetermined or preselected number of non-(n,m) chiralities.

Methods described herein, in some implementations, can thus provide highly purified populations of carbon nanotubes. However, in some cases, further separation or purification may be desired. Therefore, in some instances, methods described herein comprise separating (n,m) carbon nanotubes from non-(n,m) carbon nanotubes, non-(n,m) nanotube seeds, and/or one or more degradation products of non-(n,m) carbon nanotubes. Such separation can be performed by any method or by any means not inconsistent with the objectives of the present disclosure. For example, in some cases, gel permeation chromatography and/or nanotube-substrate registration effects can be used to separate the (n,m) carbon nanotubes from the non-(n,m) carbon nanotubes, non-(n,m) nanotube seeds, and/or one or more degradation products of non-(n,m) carbon nanotubes.

C. Methods of Making a Population of Carbon Nanotubes Selectively Depleted in (n,m) Nanotubes Alternatively, in some cases methods described herein can be used to make a population of semiconducting SWCNTs selectively depleted in (n,m) nanotubes. Such methods, in some implementations, comprise forming a plurality of non-(n,m) carbon nanotubes from the non-(n,m) nanotube seeds described in Section I.A. hereinabove. Formation of the non-(n,m) carbon nanotubes can be carried out by any methods or utilizing any apparatus not inconsistent with the objectives of the present disclosure. For example, in some implementations, non-(n,m) nanotube seeds and/or nanotubes can be heated or held within a carbon nanotube growth regime. Moreover, to provide a selectively depleted population of carbon nanotubes, methods can comprise selectively heating the (n,m) nanotube seeds described in Section I.A. to a temperature above an upper growth threshold temperature and into a carbon nanotube no growth regime. In this manner, a population of semiconducting SWCNTs selectively depleted in (n,m) nanotubes may be obtained. It is to be understood that selective heating of the (n,m) carbon nanotube seeds into a no growth regime, in some implementations, occurs concurrently with heating of the non-(n, m) nanotube seeds into a growth regime. In certain other implementations, such selective heating can occur subsequent to or prior to heating of the non-(n,m) nanotube seeds into a growth regime. FIG. 2A illustrates a chart of nanotube growth and no growth regimes as a function of temperature. As described above, an upper growth threshold temperature ($T_2$) can be a temperature at or above which carbon nanotubes form defects or do not grow into nanotubes (again, for a given set of experimental conditions). For example, in some cases, up to 100%, up to 90%, up to 80%, up to 70%, up to 60%, or up to 50% of (n,m) carbon nanotube seeds do not grow into carbon nanotubes when exposed to a temperature of $T_2$ or greater. In some instances, $T_2$ may be a temperature between about 500° C. and about 600° C. or between about 700° C. and about 800° C. As understood by one of ordinary skill in the art, however, the temperature at which a specific population of carbon nanotubes or carbon nanotube seeds may or may not grow. at a specific rate can be dependent on the experimental conditions used.

Upon completion of selective heating and/or growth in this manner, certain implementations of methods described herein can result in a bulk sample comprising non-(n,m) carbon nanotubes and (n,m) nanotube seeds. For instance, in some cases, the bulk sample comprises at least 60%, at least 70%, at least 80%, at least 90%, at least 95%, or at least 99% by mass non-(n,m) carbon nanotubes, based on the total mass of the carbon nanotubes or graphenic material formed by the method.

It is also possible, in some instances, to further purify a bulk sample formed by a method described herein. For example, in some implementations, a method described herein further comprises carrying out one or more steps to separate non-(n,m) carbon nanotubes from (n,m) nanotube seeds. Such separation can be performed by any means, methods, or apparatus not inconsistent with the objectives of the present disclosure. For example, in some implementations, separation can be carried out consistent with the above description in Section I.B. above, such as nanotube-substrate registration effects and/or gel chromatography.

As described herein, methods according to the present disclosure can be used to selectively grow a population of SWCNTs depleted in nanotubes having a desired set of (n,m) values. However, in some instances, it is possible that not all of the (n,m) nanotube seeds are limited to a no growth regime. Thus, in some cases, methods described herein further comprise forming a plurality of (n,m) carbon nanotubes from the (n,m) nanotube seeds. In such implementations, it may be desirable to deplete, reduce, or eliminate the (n,m) nanotubes. In some such instances, methods described herein further comprise selectively heating the (n,m) carbon nanotubes into a carbon nanotube degradation regime consistent with the foregoing description of degradation regimes in Section I.B. above. In some cases, selectively heating the (n,m) carbon nanotubes increases the temperature of the (n,m) carbon nanotubes by at least about 40° C., at least about 50° C., or at least about 60° C. In some instances, the temperature of the (n,m) carbon nanotubes is increased by about 40-150° C., about 50-100° C., about 50-90° C., or about 50-80° C. In certain cases, selectively heating the (n,m) carbon nanotubes can be performed in order to degrade or decompose a substantial portion of the (n,m) carbon nanotubes. Reduction of a substantial portion of the (n,m) carbon nanotubes can comprise or include degradation or decomposition of at least 50% by mass of the (n,m) carbon nanotubes, at least 60% by mass of the (n,m) carbon nanotubes, or at least 75% by mass of the (n,m) carbon nanotubes. In some instances, about 50-100%, about 50-99%, about 50-90%, about 60-95%, about 60-90%, about 60-80%, about 70-99%, about 70-90%, about 80-99%, or about 90-100% by mass of the (n,m) carbon nanotubes are degraded or decomposed. Additionally, it is to be understood that selective heating of the (n,m) carbon nanotubes can be performed to reduce or deplete carbon nanotubes having any number of predetermined or preselected (n,m) chiralities, and that such reduction or depletion can be carried out by utilizing additional laser beams and/or by selective heating of the carbon nanotubes having the predetermined or preselected number of (n,m) chiralities.

Methods described herein, in some implementations, can thus provide highly purified populations of carbon nanotubes. However, in some cases, further separation or purification may be desired. Therefore, in some instances, methods described herein comprise separating non-(n,m) carbon nanotubes from (n,m) carbon nanotubes, (n,m) nanotube seeds, and/or one or more degradation products of (n,m) carbon nanotubes. Such separation can be performed by any method or by any means not inconsistent with the objectives of the present disclosure. For example, in some cases, gel permeation chromatography and/or nanotube-substrate registration effects can be used to separate the non-(n,m) carbon nanotubes from the (n,m) carbon nanotubes, (n,m) nanotube seeds, and/or one or more degradation products of (n,m) carbon nanotubes.

D. Apparatus Usable in Methods of Making Semiconducting SWCNTs

Figure 3A:
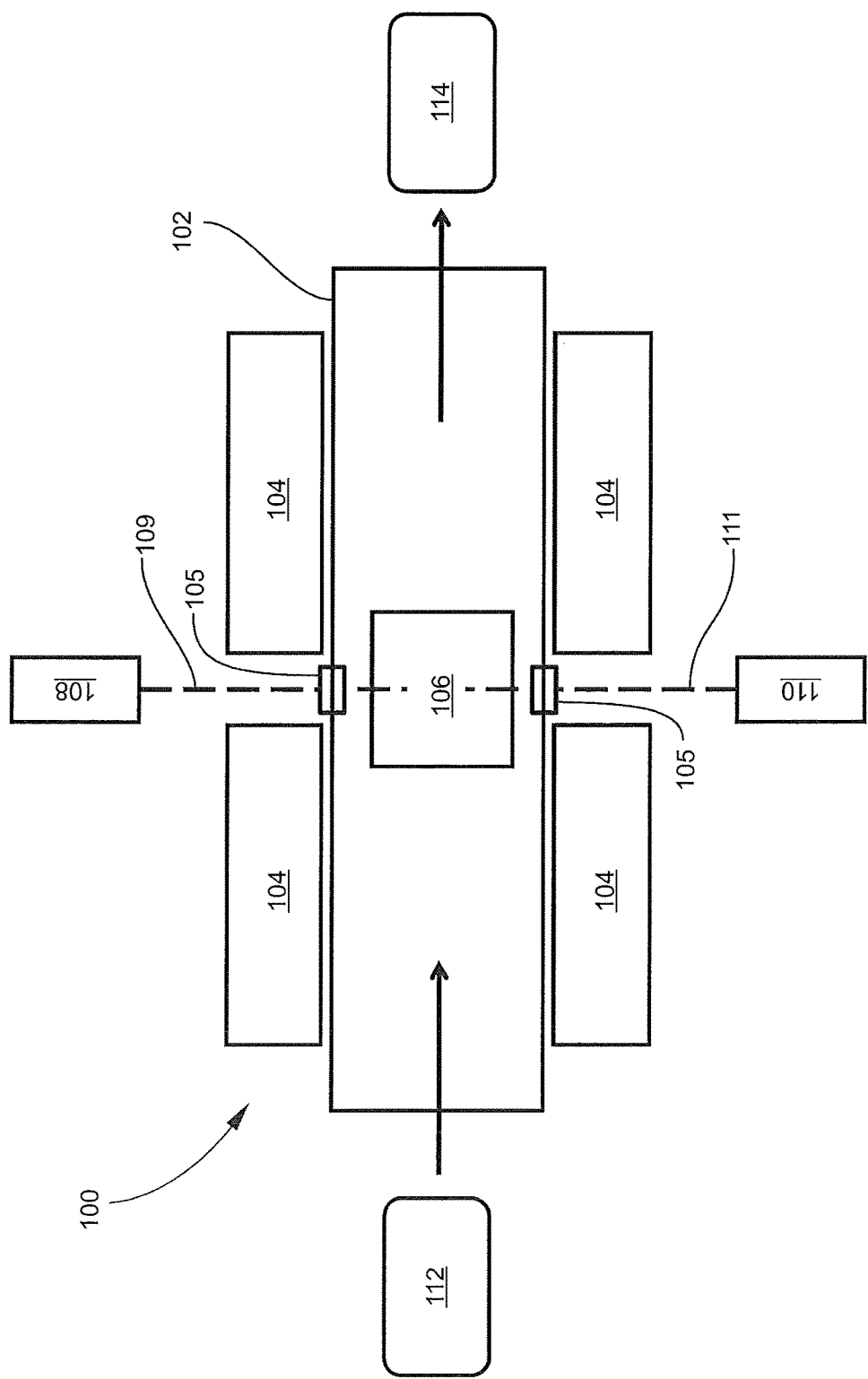
FIGS. 3A and 3B illustrate schematic representations of apparatus suitable for use in some implementations of methods described herein.
Figure 3B:
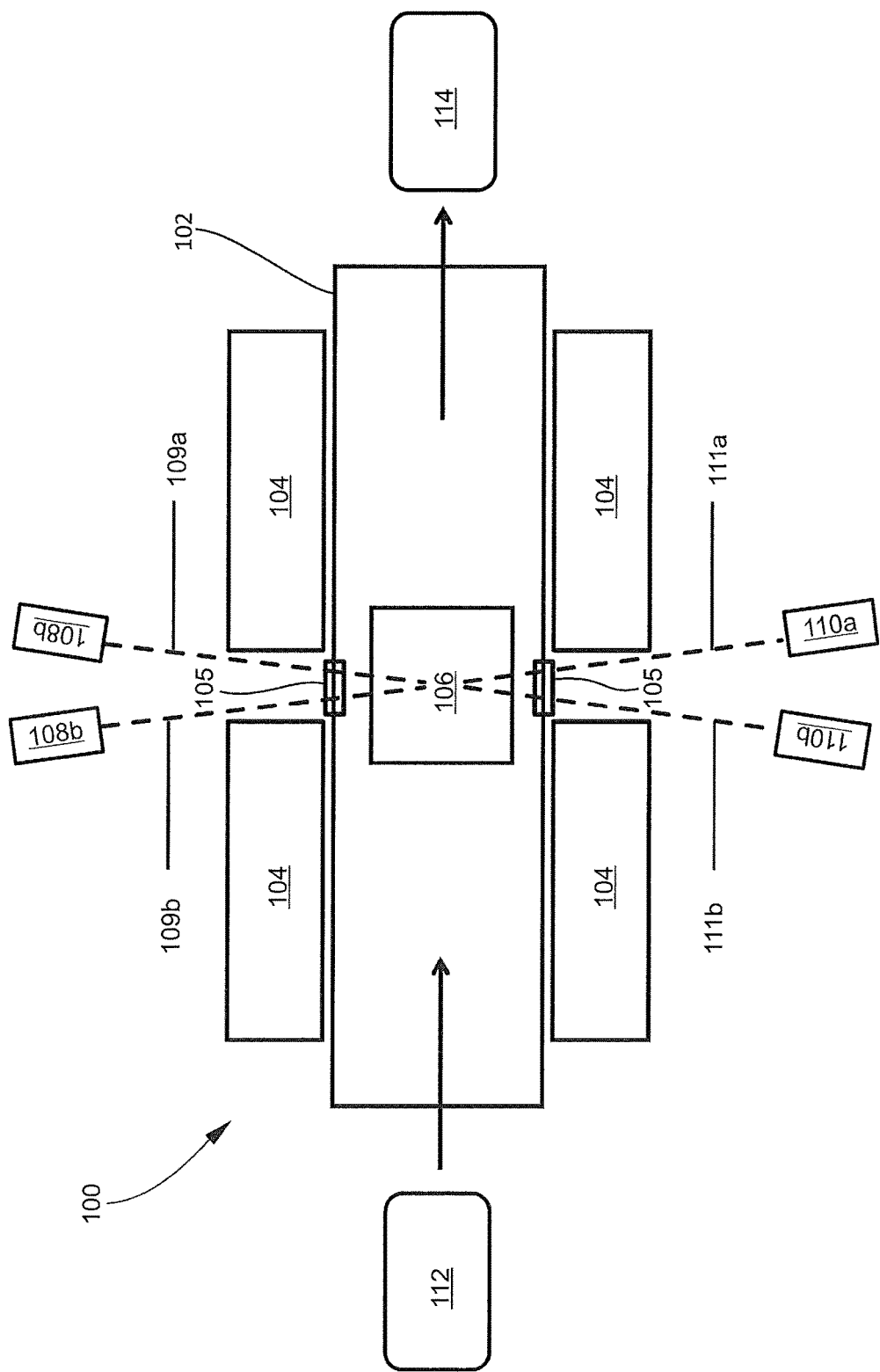

Methods of making semiconducting and/or photoluminescent SWCNTs described herein can be carried out using any apparatus not inconsistent with the objectives of the present disclosure. Two non-limiting examples of apparatus usable in such methods are illustrated schematically in FIGS. 3A and 3B. Referring to FIGS. 3A and 3B, an apparatus (100) comprises a reaction vessel, chamber, or tube (102), such as a quartz tube, in which SWCNTs can be formed. As understood by one of ordinary skill in the art, the reaction vessel (102) can be fitted or arranged such that one or more seed gases, reaction gases, and/or carrier gasses may be flowed from one end of the vessel (102) to another end of the vessel (102). For example, a seed or reaction gas (112) can be flowed through the reaction vessel (102). The seed or reaction gas (112) can comprise or consist of any materials or substances not inconsistent with the objectives of the present disclosure. For example, the seed or reaction gas (112) can comprise or consist of one or more hydrocarbon gases, and/or catalytic material. Once flowed through the reaction vessel (102), exhaust gas (114) containing the carrier gas and/or any residual unreacted or unconsumed gases or materials can exit the reaction vessel (102).

In addition, the reaction vessel (102) can be surrounded or substantially enclosed by one or more heating elements (104) such as copper tubing or a furnace. The heating elements can be used to achieve or maintain a desired temperature of the seed gas (112) and/or the reaction vessel (102). As described hereinabove, it is also possible to at least partially control the temperature of the reaction vessel (102) and/or of one or more materials within the reaction vessel (102) by supplying the seed gas (112) at a desired temperature.

Further, one or more windows (105) can be provided in the vessel (102) to permit light to enter the interior of the vessel (102). As illustrated in FIGS. 3A and 3B, the reaction vessel (102) includes two windows (105). However, other numbers of windows may also be used. Moreover, a window (105) can be formed by an optically transparent material (such as a glass) or by a gap in the heating elements (104), provided that the window (105) permits light of a desired wavelength to be transmitted into the interior of the reaction vessel (102), such as a plurality of laser beams (109, 111) produced by a plurality of lasers (108, 110). Additionally, as illustrated in FIGS. 3A and 3B, the windows (105) are arranged to permit illumination of a sample substrate (106) disposed within the reaction vessel (102). The sample substrate (106) can be formed of any material not inconsistent with the objectives of the present disclosure. For example, in some implementations, the sample substrate (106) comprises or is formed from a catalytic material.

In the implementation illustrated in FIG. 3A, the sample substrate (106), which may have a plurality of nanotube seeds or nanotubes disposed thereon, can be illuminated by a first laser beam (109) emitted by a first laser (108) and a second laser beam (111) emitted by a second laser (110). In the implementation illustrated in FIG. 3B, the sample substrate (106) can be illuminated by a first laser beam (109a) emitted by a first laser (108a), a second laser beam (111a) emitted by a second laser (110a), a third laser beam (109b) emitted by a third laser (108b), and a fourth laser beam (111b) emitted by a fourth laser (110b).

Other apparatus may also be used to carry out a method described herein.

II. Methods of Purifying a Population of Semiconducting SWCNTs

In another aspect, methods of purifying a population of carbon nanotubes are described herein. In some implementations, methods described herein comprise providing a population of carbon nanotubes, such as a population of semiconducting or photoluminescent SWCNTs, including (n,m) carbon nanotubes and non-(n,m) carbon nanotubes. The methods further comprise illuminating the population of carbon nanotubes with a first laser beam having a first wavelength and a second laser beam having a second wavelength, the second wavelength differing from the first wavelength. The first wavelength corresponds to an absorption maximum of the (n,m) carbon nanotubes, and the second wavelength corresponds to a photoluminescence emission frequency of the (n,m) carbon nanotubes. Additionally, in some cases, methods of purifying a population of carbon nanotubes further comprise selectively heating the (n,m) carbon nanotubes into a carbon nanotube degradation regime. In some such implementations, the non-(n,m) carbon nanotubes are not heated into the carbon nanotube degradation regime. Moreover, methods of purifying a population of carbon nanotubes described herein, in some cases, degrade or decompose at least about 50%, at least about 60%, or at least about 75% by mass of the (n,m) carbon nanotubes present, based on the total weight of the (n,m) carbon nanotubes. In some instances, methods described herein degrade or decompose about 50-100%, about 50-99%, about 50-90%, about 60-95%, about 60-90%, about 60-80%, about 70-99%, about 70-90%, about 80-99%, or about 90-100% by mass of the (n,m) carbon nanotubes.

Turning now to specific steps of methods described herein, purifying a population of carbon nanotubes, such as semiconducting SWCNTs or photoluminescent SWCNTs, comprises providing a population of carbon nanotubes. The population of carbon nanotubes can be provided or formed by any means or by any method not inconsistent with the objectives of the present disclosure. For example, in some implementations, the population of carbon nanotubes is provided or formed by a method described in Section I hereinabove. Further, in some cases, the population of carbon nanotubes can be provided or formed from at least one method selected from the group consisting of catalyst assisted chemical vapor deposition (CVD), high-pressure CO gas decomposition, arc discharge, laser ablation, and direct injection pyrolytic synthesis.

Methods described herein also comprise illuminating the population of carbon nanotubes with a first laser beam having a first wavelength and a second laser beam having a second wavelength, wherein the first wavelength corresponds to an absorption maximum of the (n,m) carbon nanotubes and the second wavelength corresponds to a photoluminescence emission frequency of the (n,m) carbon nanotubes. Absorption maxima and/or photoluminescence emission frequencies, such as peak emission frequencies, can be selected or determined by any means not inconsistent with the objectives of the present disclosure. For example, in some implementations, a photoluminescence map described hereinabove in Section I may be used. In addition, as described further hereinabove in Section I, multiple (n,m) carbon nanotubes may be selectively depleted from a population of carbon nanotubes according to a method described herein. In such instances, additional laser beams with differing wavelengths can be used to illuminate the population of carbon nanotubes. For example, in the event that two types of (n,m) carbon nanotubes with differing sets of (n,m) values are preselected for depletion, a third laser beam having a third wavelength and a fourth laser beam having a fourth wavelength can also be used, the fourth wavelength differing from the third wavelength. The third wavelength can correspond to an absorption maximum for a second (n,m) carbon nanotube, and the fourth wavelength can correspond to a photoluminescence emission frequency for the second (n,m) carbon nanotube. Moreover, the same principle can be used to selectively deplete a population of carbon nanotubes of more than two differing types of (n,m) carbon nanotubes. In general, to selectively deplete a population of carbon nanotubes of x differing types of (n,m) carbon nanotubes, x pairs of laser beams having wavelengths selected in a manner described above can be used.

In addition, methods described herein can further comprise selectively heating (n,m) carbon nanotubes into a carbon nanotube degradation regime. Again not intending to be bound by theory, and as described hereinabove in Section I, it is believed that such heating can be achieved by creating resonance between energy states of preselected carbon nanotubes. Moreover, in some cases, (n,m) carbon nanotubes are selectively heated to increase the temperature of the (n,m) carbon nanotubes by at least about 40° C., at least about 50° C., or at least about 60° C. In some cases, the temperature of the (n,m) carbon nanotubes is increased by about 40-150° C., about 50-100° C., about 50-90° C., or about 50-80° C. Additionally, selective heating of the (n,m) carbon nanotubes can be performed in a manner such that the non-(n,m) carbon nanotubes are not heated into the carbon nanotube degradation regime. In such cases, any residual heat absorbed by or applied to the non-(n,m) carbon nanotubes should be insufficient to raise the temperature of the non-(n,m) carbon nanotubes into the carbon nanotube degradation regime. For example, the non-(n,m) carbon nanotubes can exhibit a temperature increase of less than 50° C.

As described hereinabove, methods of purifying a population of carbon nanotubes can provide a population of carbon nanotubes that are highly depleted in nanotubes having one or more preselected (n,m) values. However, in the event that further purification or separation is desired, methods described herein can further comprise separating residual (n,m) carbon nanotubes from the remainder of the population of carbon nanotubes, such as non-(n,m) carbon nanotubes that may be present, following selective heating. Such separation can be performed by any means or by any methods not inconsistent with the objectives of the present disclosure, such as a method described hereinabove in Section I.

In addition, methods of purifying a population of carbon nanotubes, such as semiconducting SWCNTs, can be performed within or utilizing any apparatus not inconsistent with the objectives of the present disclosure. For example, an apparatus described hereinabove in Section I may be used.

III. Compositions

In another aspect, compositions are described herein. Compositions described herein, in some cases, can be made by a method described hereinabove in Section I and/or Section II. Thus, in some implementations, compositions described herein are enriched or are substantially enriched in semiconducting SWCNTs having one or more predetermined or preselected chiralities. For example, a composition described herein can, in some cases, comprise or include at least 90% by mass, at least 95% by mass, at least 99% by mass, or at least 99.9% by mass of semiconducting SWCNTs having one or more predetermined or preselected chiralities. In some instances, a composition comprises or includes about 50-100%, about 50-90%, about 60-100%, about 60-99%, about 60-90%, about 70-100%, about 70-99%, about 70-90%, about 75-100%, about 75-95%, about 80-100%, about 80-99%, about 80-90%, about 90-100%, or about 90-99% by mass of semiconducting SWCNTs having one or more predetermined or preselected chiralities. The nanotubes having one or more predetermined or preselected chiralities in which the sample can be enriched can be selected from nanotubes having (n,m) values selected from the group consisting of (10,3), (9,4), (8,6), (12,1), (11,3), (8,7), (10,5), (9,7), (13,2), (12,4), (11,4), (10,6), (9,8), (11,6), (14,1), (13,3), (12,5), (11,7), (10,8), (15,1), (14,3), (13,5), (10,9), (12,7), (16,2), (15,4), (15,2), (14,4), (13,6), (12,8), (11,9), (14,6), (17,1), (16,3), (15,5), (14,7), (11,10), (13,8), and (13,9). In addition, in some instances, a composition can be enriched in nanotubes having more than one of the (n,m) values described above, as described further hereinabove in Section I. Compositions described herein can thus comprise many unique combinations of carbon nanotubes having preselected (n,m) values. Moreover, such compositions can be derived from a single reaction vessel or reaction, as opposed to being provided by combining separately made carbon nanotubes.

In addition, in other implementations, compositions described herein can be depleted or substantially depleted in nanotubes having one or more predetermined or preselected chiralities. For example, a composition described herein can, in some cases, comprise or include less than 50% by mass, less than 40% by mass, less than 30% by mass, less than 15% by mass, less than 10% by mass, less than 5% by mass, less than 1% by mass, or less than 0.01% by mass of SWCNTs having one or more predetermined or preselected chiralities. The nanotubes having one or more predetermined or preselected chiralities in which the sample can be depleted can be selected from nanotubes having (n,m) values selected from the group consisting of (10,3), (9,4), (8,6), (12,1), (11,3), (8,7), (10,5), (9,7), (13,2), (12,4), (11,4), (10,6), (9,8), (11,6), (14,1), (13,3), (12,5), (11,7), (10,8), (15,1), (14,3), (13,5), (10,9), (12,7), (16,2), (15,4), (15,2), (14,4), (13,6), (12,8), (11,9), (14,6), (17,1), (16,3), (15,5), (14,7), (11,10), (13,8), and (13,9). In addition, in some instances, a composition can be depleted in nanotubes having more than one of the (n,m) values described above, as described further hereinabove in Section I and Section II.

Moreover, in some implementations, a composition described herein is enriched or substantially enriched in one or more of the foregoing nanotubes and is depleted or substantially depleted in one or more of the foregoing nanotubes. A composition can be enriched and depleted in any combination of carbon nanotubes described hereinabove not inconsistent with the objectives of the present disclosure.

In addition, compositions described herein can be formed by any means, methods, or apparatus not inconsistent with the objectives of the present disclosure. For example, in some implementations, enriched or substantially enriched and/or depleted or substantially depleted compositions described herein can be formed or provided by methods described hereinabove in Section I and/or Section II.

Various implementations of the disclosure have been described in fulfillment of the various objectives of the disclosure. It should be recognized that these implementations are merely illustrative of the principles of the present disclosure. Numerous modifications and adaptations thereof will be readily apparent to those skilled in the art without departing from the spirit and scope of the disclosure.

That which is claimed is:

1. A method of purifying a population of carbon nanotubes comprising:
   illuminating a population of carbon nanotubes including semiconducting (n,m) carbon nanotubes and non-(n,m) carbon nanotubes with a first laser beam having a first wavelength and a second laser beam having a second wavelength, the second wavelength differing from the first wavelength;
   selectively heating the (n,m) carbon nanotubes into a carbon nanotube degradation regime; and
   growing the non-(n,m) carbon nanotubes in a carbon nanotube growth regime,
   wherein the carbon nanotubes were grown from carbon nanotube seeds;
   wherein the first wavelength corresponds to an absorption maximum of the (n,m) carbon nanotubes;
   wherein the second wavelength corresponds to a photoluminescence emission frequency of the (n,m) carbon nanotubes; and
   wherein the non-(n,m) carbon nanotubes are not heated into the carbon nanotube degradation regime but instead occupy the carbon nanotube growth regime.

2. The method of claim 1, wherein the (n,m) carbon nanotubes are selectively heated to increase the temperature of the (n,m) carbon nanotubes by at least 50° C.

3. The method of claim 1, wherein at least 60% by mass of the (n,m) carbon nanotubes are degraded or decomposed.

4. The method of claim 1, wherein at least 75% by mass of the (n,m) carbon nanotubes are degraded or decomposed.

5. The method of claim 1, further comprising separating the non-(n,m) carbon nanotubes from the (n,m) carbon nanotubes and/or from one or more degradation products of the (n,m) carbon nanotubes.

6. The method of claim 1, wherein the photoluminescence emission frequency comprises a photoluminescence emission peak.

7. The method of claim 1, wherein the selective heating of the (n,m) carbon nanotubes causes residual heat to be absorbed by or applied to the non-(n,m) carbon nanotubes, and wherein the residual heat is insufficient to raise the temperature of the non-(n,m) carbon nanotubes into the carbon nanotube degradation regime.

8. The method of claim 1, further comprising separating residual (n,m) carbon nanotubes from the non-(n,m) carbon nanotubes after the selective heating.

9. A method of purifying a population of carbon nanotubes comprising:
  illuminating a population of carbon nanotubes including semiconducting first (n,m) carbon nanotubes, second (n,m) carbon nanotubes, and non-(n,m) carbon nanotubes with a first laser beam having a first wavelength, a second laser beam having a second wavelength, a third laser beam having a third wavelength, and a fourth laser beam having a fourth wavelength;
  selectively heating the first (n,m) carbon nanotubes into a carbon nanotube degradation regime; and
  growing the non-(n,m) carbon nanotubes in a carbon nanotube growth regime,
  wherein the carbon nanotubes were grown from carbon nanotube seeds;
  wherein the first (n,m) carbon nanotubes and the second (n,m) carbon nanotubes have differing sets of (n,m) values;
  wherein the first wavelength corresponds to an absorption maximum of the first (n,m) carbon nanotubes;
  wherein the second wavelength corresponds to a photoluminescence emission frequency of the first (n,m) carbon nanotubes;
  wherein the second wavelength differs from the first wavelength;
  wherein the third wavelength corresponds to an absorption maximum of the second (n,m) carbon nanotubes;
  wherein the fourth wavelength corresponds to a photoluminescence emission frequency of the second (n,m) carbon nanotubes;
  wherein the fourth wavelength differs from the third wavelength; and
  wherein the non-(n,m) carbon nanotubes are not heated into the carbon nanotube degradation regime but instead occupy the carbon nanotube growth regime.

* * * * *